(12) United States Patent
Kim et al.

(10) Patent No.: US 7,433,032 B2
(45) Date of Patent: Oct. 7, 2008

(54) METHOD AND APPARATUS FOR INSPECTING DEFECTS IN MULTIPLE REGIONS WITH DIFFERENT PARAMETERS

(75) Inventors: Joung-Soo Kim, Gyeonggi-do (KR); Sang-Mun Chon, Gyeonggi-do (KR); Chung-Sam Jun, Gyeonggi-do (KR); Yu-Sin Yang, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 234 days.

(21) Appl. No.: 11/253,028

(22) Filed: Oct. 17, 2005

(65) Prior Publication Data

US 2006/0082766 A1    Apr. 20, 2006

(30) Foreign Application Priority Data

Oct. 19, 2004   (KR) .................... 10-2004-0083401

(51) Int. Cl.
*G01B 15/00* (2006.01)
*G01N 21/00* (2006.01)

(52) U.S. Cl. .............. 356/237.2; 356/394; 356/398; 382/144; 382/145

(58) Field of Classification Search ............. 356/237.2, 356/394, 398, 144, 145
See application file for complete search history.

(56) References Cited

U.S. PATENT DOCUMENTS

| 6,437,862 B1 * | 8/2002 | Miyazaki et al. ......... 356/237.2 |
| 6,614,519 B1 * | 9/2003 | Latta et al. ............... 356/237.2 |
| 6,850,320 B2 * | 2/2005 | Shibata et al. ........... 356/237.3 |
| 2003/0223058 A1 * | 12/2003 | Leong et al. ............ 356/237.2 |
| 2004/0057611 A1 * | 3/2004 | Lee et al. ..................... 382/145 |
| 2004/0105578 A1 * | 6/2004 | Tsuchiya et al. ........... 382/144 |
| 2004/0169850 A1 * | 9/2004 | Meeks ...................... 356/237.2 |

FOREIGN PATENT DOCUMENTS

| JP | 2002-148031 | * 5/2002 |
| KR | 2003-49312 | 6/2003 |
| KR | 2003-52657 | 6/2003 |

OTHER PUBLICATIONS

English language abstract of Japanese Publication No. 2002-148031.
English language abstract of Korean Publication No. 2003-49312.
English language abstract of Korean Publication No. 2003-52657.

* cited by examiner

*Primary Examiner*—L. G. Lauchman
*Assistant Examiner*—Rebecca C Slomski
(74) *Attorney, Agent, or Firm*—Marger Johnson & McCollom, P.C.

(57) ABSTRACT

In a method of inspecting defects, a first actual region of an actual object is inspected based on a first characteristic parameter as an inspection condition. A point where an inspection region of the actual object is changed into a second actual region from the first actual region is determined. The second actual region is then inspected based on a second characteristic parameter as the inspection condition. The first and second parameters may include contrast of a light that is reflected from a reference object, intensity of the light, brightness of the light, a size of a minute structure on the reference object, etc. The characteristic parameters of each reference region on the reference object are set. Thus, the defects may be accurately classified so that a time and a cost for reviewing the defects may be markedly reduced.

24 Claims, 7 Drawing Sheets

METHOD AND APPARATUS FOR INSPECTING DEFECTS IN MULTIPLE REGIONS WITH DIFFERENT PARAMETERS

BACKGROUND OF THE INVENTION

1. Cross-References to Related Applications

This application claims priority under 35 USC § 119 to Korean Patent Application No. 2004-83401, filed on Oct. 19, 2004, the contents of which are herein incorporated by reference in its entirety for all purposes.

2. Field of the Invention

The present invention relates to a method of inspecting defects and an apparatus for performing the same. More particularly, the present invention relates to a method of inspecting defects that is capable of detecting the defects on a precision object such as a semiconductor substrate and then classifying the defects, and an apparatus for performing the method.

3. Description of the Prior Art

Continued improvements in semiconductor design and manufacturing result in devices having ever increasing integration and capacity. Such devices require extremely accurate thin layer patterns to be formed on the semiconductor substrate, and such accuracy is determined by inspecting the resulting pattern formed. For example, after a pattern is formed on a semiconductor substrate, defects such as particles or micro-scratches may be generated on the pattern. Planarization of the pattern by a chemical mechanical polishing (CMP) process may also generate the above-mentioned defects on the pattern.

As both the size of the semiconductor substrates increase and devices using such substrates become more highly integrated, increasing numbers of inspection regions are required to be tested on a single semiconductor wafer. In the past, tens of inspection regions would be set on a single semiconductor substrate, and tens of defects on the semiconductor substrate detected. With increased integration, however, hundreds to thousands of inspection regions are set on a single semiconductor substrate resulting in hundreds to thousands of defects detected on the semiconductor substrate. The increased number of required inspections has resulted in a skyrocketing time to complete the inspection of the semiconductor devices.

FIG. 1 is a flow chart illustrating a conventional method of inspecting defects.

Referring to FIG. 1, in step S11, a semiconductor substrate is scanned using a defect inspection tool to obtain information about the semiconductor substrate. In step S13, the information is converted into a digital signal and, in step S15, the digital signal is stored in a server. In step S17, defects on the semiconductor substrate are detected and classified based on the digital signal. In step S19, the number of the defects is accumulated to determine whether it is beyond a predetermined allowable number or, in the alternative, whether critical defects are recognized on the semiconductor substrate.

When the number of the defects is beyond the allowable number or critical defects are found on the semiconductor substrate, in step S21, the semiconductor substrate is manually/visually inspected with the help of a reviewing tool such as a microscope, a scanning electron microscope (SEM), etc., to recognize the configuration, shape, and kind of the defect. Critical defects are recognized during this manual inspection process.

Whether the defects are found during the reviewing steps to be normal or critical determine whether following process steps are carried out. When the defects are determined to be normal, in step S25, the subsequent process is carried out. On the other hand, when the defects are determined to be abnormal, in step S27, the subsequent process is not performed on the semiconductor substrate. Instead, the process is suspended and the apparatus used for a preceding process (and being the potential cause of the defect formation) is then repaired as required.

Critical defects are primarily recognized using a defect-classifying program. The defect-classifying program classifies the detected defects based on parameters such as a contrast, an intensity, a size, etc. Here, the parameters correspond to reference values for processing the information of the detected defects.

FIG. 2 is a graph illustrating a typical inspection result obtained using the conventional method. In FIG. 2, a vertical axis represents the contrast and a horizontal axis represents the intensity. Values of the contrast and the intensity in FIG. 2 are expressed as conversion units.

As shown in FIG. 2, defects having diverse contrasts and intensities are shown to exist on the semiconductor substrate. It has been found, however, that defects with diverse contrasts and intensities may actually be of a similar type and that those defects with similar contrasts and intensities may in fact be quite different types of defects—a fact that cannot be determined from a simple inspection of the conventional contrast/intensity plot as shown in FIG. 2. That is, defects having the above-mentioned conditions are not adequately distinguished from each other.

It is particularly important to accurately classify the defects by accurately distinguishing between intrinsic signals of the defects and background signals of a region where the defects exist. Here, a standard for distinguishing between the intrinsic signals of the defects and the background signals of the region corresponds to a parameter. The parameter for distinguishing the intrinsic signals of the defects varies in accordance with kinds of the background signals. For example, to accurately inspect particles on a cell region of a semiconductor substrate, a contrast is an optimal parameter. Also, to accurately inspect particles on a peripheral region of the semiconductor substrate, an intensity is an optimal parameter.

According to the conventional method, since the defects detected from entire regions of a semiconductor substrate are classified based on the same parameters, the conventional defect classification has a very low accuracy. Thus, defect inspection under the conventional method requires a further manual inspection to determine whether the critical defects found would be of the type that would influence subsequent processing or operation. Accordingly, the time required to conduct inspections of the devices increases thus also increasing a cost for manufacturing the semiconductor device.

To overcome the above-mentioned problems, a method of classifying defects is disclosed in Japanese Patent Laid Open Publication No. 2004-148031. In the method of classifying defects, characteristic parameters by densities of patterns on each region of a semiconductor substrate are set. Defects in regions that have densities substantially similar to each other are then classified as a same defect. An image of the semiconductor substrate is obtained using an SEM, a typically time intensive procedure. The defects in the regions having the similar densities are detected from the image and are then classified as the same defect based on the characteristic parameters. That is, since the SEM is used in the conventional method, efficiency for detecting defects is very low. And although the regions have similar densities, the regions may in fact have different kinds defects so that the defect classification is relatively inaccurate. Regions having the similar densities but different defect types may have different background signals. As a result, parameters for inspecting the defects in the regions may be different from each other. Further, to effectively inspect the defect, different parameters may be employed in the inspection process in accordance with the kinds of the defects in the regions having the similar densities. Thus, a reviewing of the defects is required in the conventional method resulting in the original problem.

Accordingly, the need remains for an inspection tool and method for more accurately and quickly detecting and classifying defects that occur on semiconductor devices during manufacturing.

SUMMARY OF THE INVENTION

The present invention provides a method of inspecting defects that is capable of reducing a reviewing time by more accurately classifying the defects on an object without the use of a subsequent inspection tool.

The present invention also provides an apparatus for performing the above-mentioned method.

As applied to the specific instance of inspection of a semiconductor substrate for defects, the inventive method comprises illuminating a first irradiation point on the semiconductor substrate located within a first region of the semiconductor substrate. Light (e.g. reflected and/or scattered) is then collected from the first irradiation point and analyzed based on a first characteristic parameter associated with the first region inspected to determine whether an abnormal defect exists at the first irradiation point. The irradiation point is then moved to a second irradiation point located within a second region of the semiconductor substrate and light collected from the second irradiation point. The collected light is then analyzed from the second irradiation point based on a second characteristic parameter, different from the first characteristic parameter, associated with the second region. This analysis can then determine whether an abnormal defect exists at the second irradiation point based.

More generally, and in a method of inspecting defects on an object in accordance with one aspect of the present invention, a first actual region of an actual object is inspected based on a first characteristic parameter as an inspection condition. A point where an inspection region of the actual object is changed into a second actual region from the first actual region is determined. The second actual region is then inspected based on a second characteristic parameter as the inspection condition.

According to one embodiment, the first and second parameters may include contrast of a light that is reflected from a reference object, intensity of the light, brightness of the light, a size of a minute structure on the reference object, etc. Also, the first characteristic parameter is obtained by inspecting defects on a first reference region of the reference object. The second characteristic parameter is obtained by inspecting defects on a second reference region of the reference object. Further, the first actual region is positioned on first coordinates substantially identical to that of the first reference region. The second actual region is positioned on second coordinates substantially identical to that of the second reference region.

An apparatus for inspecting defects on an object in accordance with another aspect of the present invention includes a scanning unit for scanning an actual object, which is divided into at least two actual regions, using a light to obtain information of the actual regions, respectively. A determining unit determines a point where an actual region receiving the light is changed into an adjacent actual region. An inspecting unit inspects the information based on predetermined characteristic parameters to detect and classify defects on the object.

According to one embodiment, the determining unit includes a storing unit for storing the characteristic parameters that are obtained by inspecting a reference object by each reference region.

According to the present invention, after the characteristic parameters of each reference region on the reference object are set, the actual regions of the actual object are inspected based on the characteristic parameters to accurately detect and classify the defects on the actual object. Thus, a time for reviewing the defects may be remarkably reduced.

BRIEF DESCRIPTION OF THE DRAWINGS

The above and other features and advantages of the invention will become readily apparent by reference to the following detailed description when considered in conjunction with the accompanying drawings wherein.

DESCRIPTION OF THE EMBODIMENTS

Figure 1:
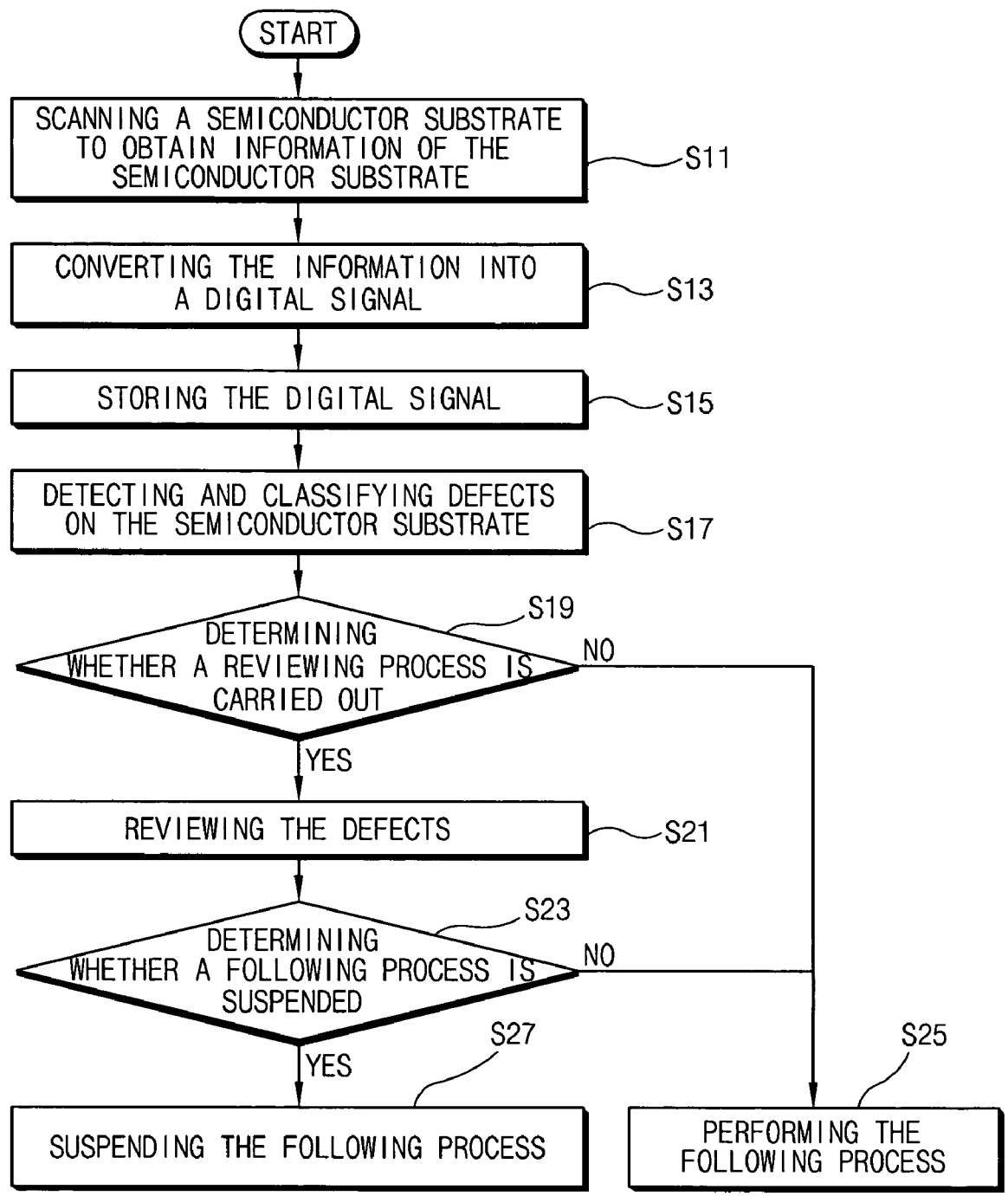
FIG. 1 is a flow chart illustrating a conventional method of inspecting defects.
Figure 2:
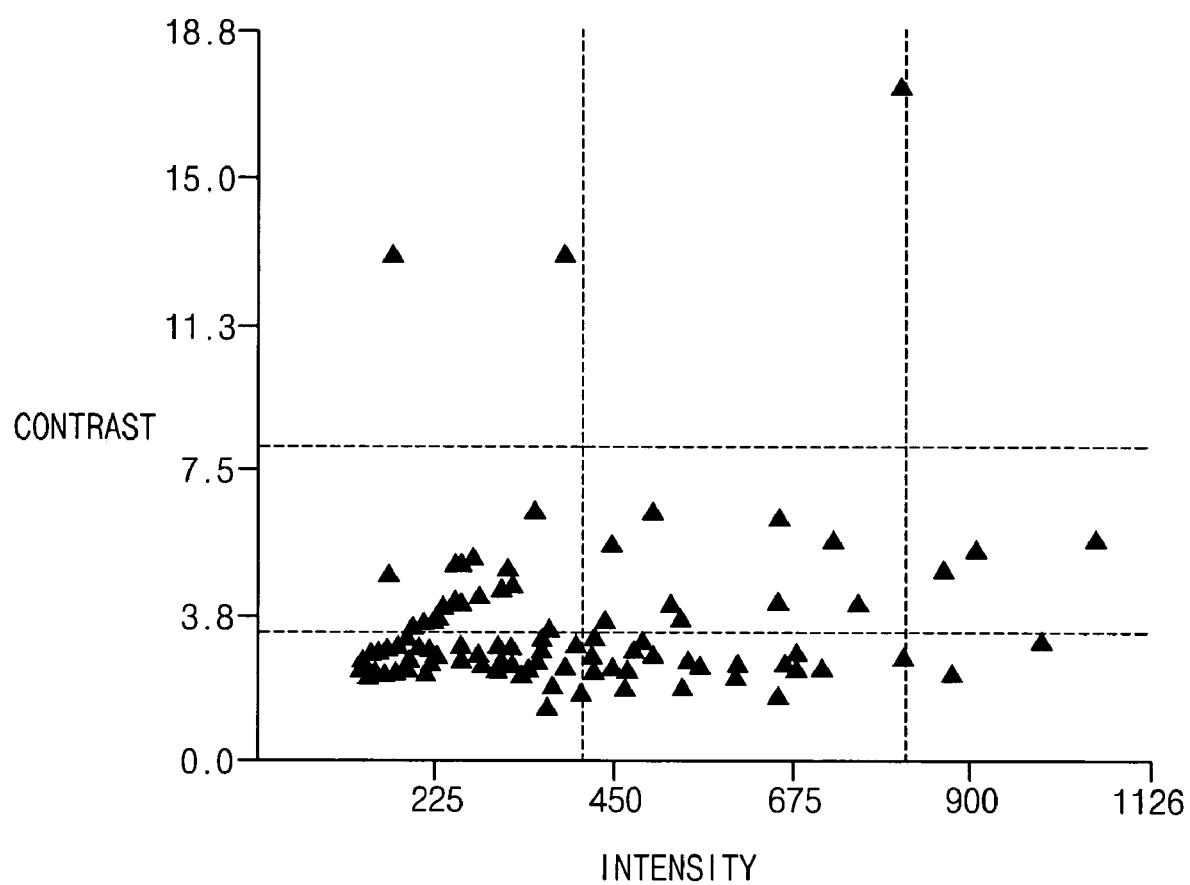
FIG. 2 is a graph illustrating an inspection result of a semiconductor substrate using the conventional method in FIG. 1.

The present invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the sizes and relative sizes of layers and regions may be exaggerated for clarity.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 3:
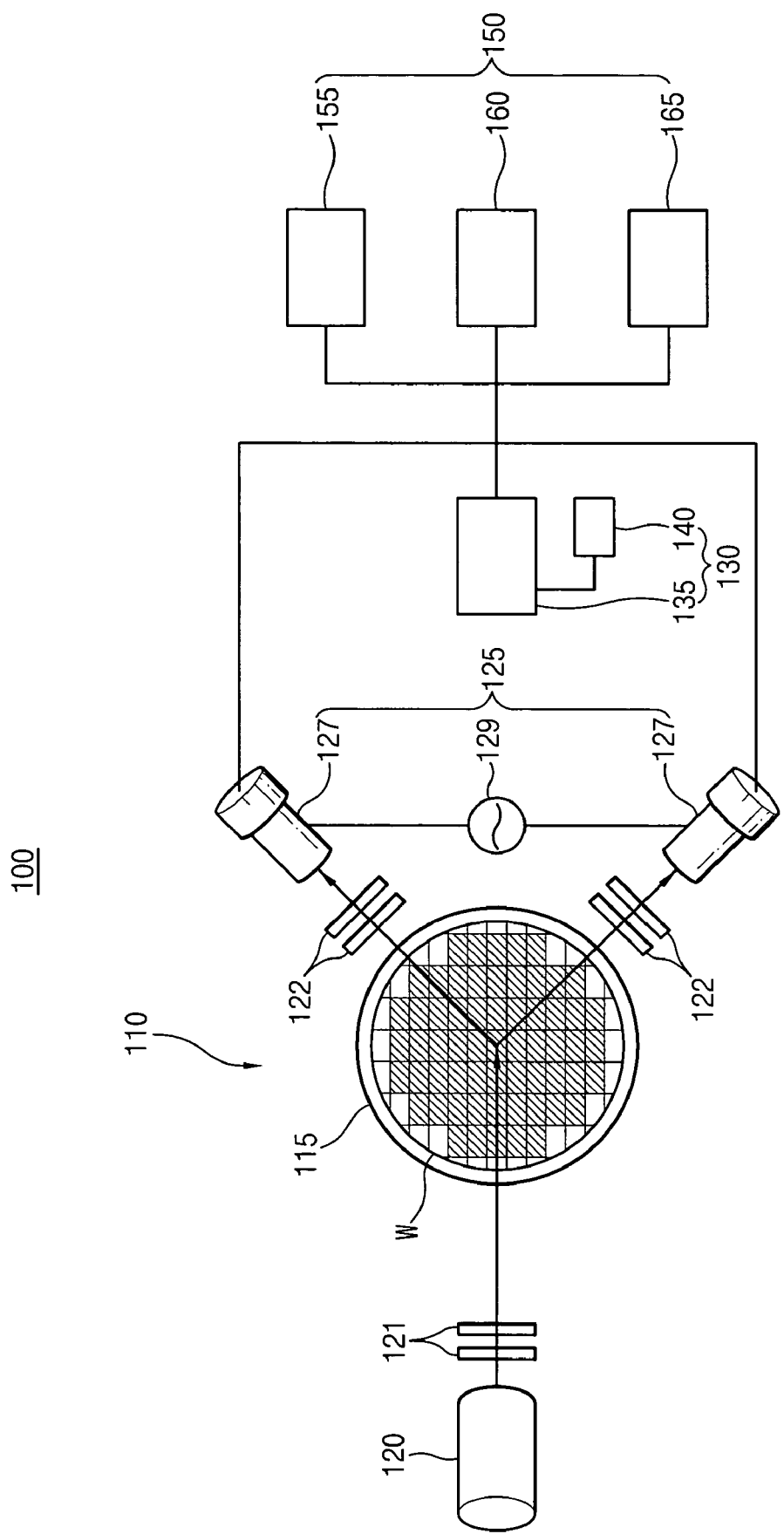
FIG. 3 is a block diagram illustrating an apparatus for inspecting defects in accordance with an exemplary embodiment of the present invention.
Figure 4:
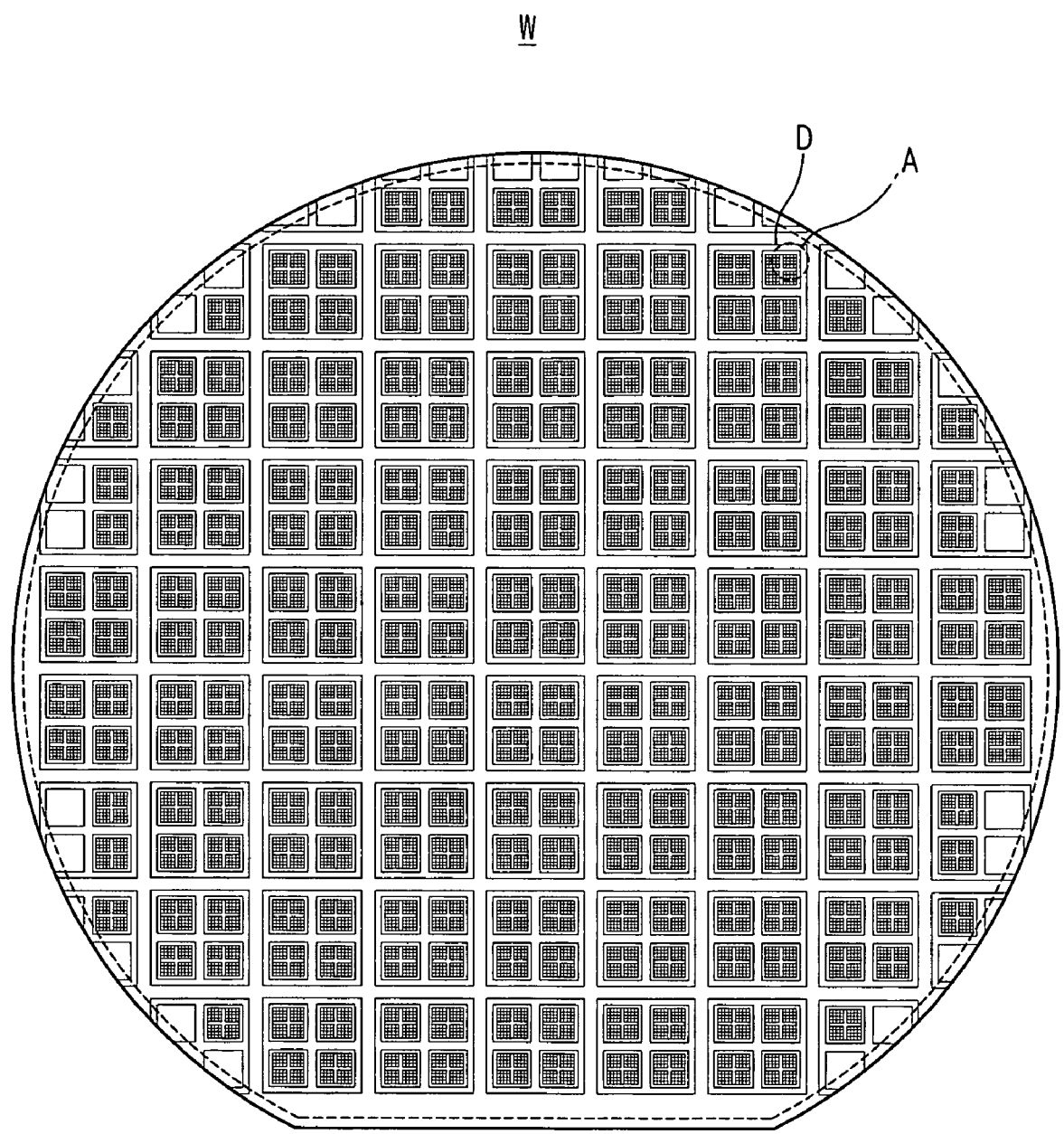
FIG. 4 is an enlarged plan view illustrating a semiconductor substrate in FIG. 3.

FIG. 3 is a block diagram illustrating an apparatus for inspecting defects in accordance with an exemplary embodiment of the present invention, and FIG. 4 is an enlarged plan view illustrating a semiconductor substrate in FIG. 3.

Referring to FIGS. 3 and 4, an apparatus 100 as shown in FIGS. 3 and 4 includes a scanning unit 110, a determining unit 130 and an inspecting unit 150. The scanning unit 110 irradiates a light onto an object, for example, a semiconductor substrate W, which is divided into a plurality of inspection regions, to scan the semiconductor substrate W. The determining unit 130 determines a point where the inspection region is changed into an adjacent inspection region in scanning the semiconductor substrate W. The inspecting unit 150 inspects information of each inspection region scanned by the light based on each characteristic parameter, respectively, to detect defects on the semiconductor substrate and then classify the defects.

The scanning unit 110 includes a stage 115, a light emitter 120 and a light receiver 125.

The stage 115 is positioned at a central portion of the apparatus 100. The stage 115 supports and transfers the semiconductor substrate W. The semiconductor substrate W on the stage 115 is transferred in a horizontal direction.

The light emitter 120 is placed over and adjacent to the semiconductor substrate W on the stage 115. The light emitter 120 emits the light onto the semiconductor substrate W. The light emitted from the light emitter 120 may include a laser having a wavelength of about 488 nm. Alternatively, other light emitters for emitting a different light having a different wavelength may be employed in the scanning unit 110. Persons skilled in the art may readily exchange the light emitter 120 for other light emitters in accordance with kinds of the objects or inspection conditions.

The light emitter 120 may be arranged in a direction substantially perpendicular to a surface of the semiconductor substrate W or in a direction inclined to the surface of the semiconductor substrate W. In the present embodiment, the light emitter 120 is arranged at an angle of about 20° to about 70° with respect to the surface of the semiconductor substrate W. Thus, the light having an incident angle of about 20° to about 70° with respect to the surface of the semiconductor substrate W is irradiated onto the surface of the semiconductor substrate. Additionally, a light path-changing unit (not shown) for changing a path of the light may be arranged between the light emitter 120 and the semiconductor substrate W.

A first polarizer 121 is placed between the light emitter 120 and the semiconductor substrate W. The first polarizer 121 includes a polarizing plate such as a plate having a ½ wavelength or a ¼ wavelength. The first polarizer 121 converts the light into a polarized light such as a primary (P) polarized light, a secondary (S) polarized light, a circular (C) polarized light or a combination thereof. Thus, the polarized light is irradiated onto the semiconductor substrate W and is then reflected or scattered from the semiconductor substrate. Here, the reflected or scattered light may have a reflection angle substantially identical to or different from the incident angle.

The light receiver 125 receives the reflected or scattered light. The light receiver 125 includes a photomultiplier tube 127 and a power supply 129. The photomultiplier tube 127 collects the reflected or scattered light and then amplifies the collected light by an amplification ratio. The power supply 129 applies an operation voltage to the photomultiplier tube 127.

Here, the reflected or scattered light has a very low intensity. Thus, the photomultiplier tube 127 amplifies the reflected or scattered light by an amplification ratio to increase an output signal. In particular, the reflected or scattered light is reacted with a photocathode of the photomultiplier tube 127 to generate photoelectrons. The photoelectrons pass through dynodes to which gradually increased voltages are sequentially applied so that the photoelectrons are amplified, thereby creating the increased output signal.

The photomultiplier tube 127 measures a single photon. Also, the photomultiplier tube 127 measures a dark current of about 0.3 pA that has a band of about 0.2 μm to about 1.1 μm so that the photomultiplier tube 127 may be effectively used for detecting the defects. Alternatively, other light receivers such as a charge-coupled device (CCD) camera may be used. In the apparatus as shown in FIGS. 3 and 4, the light receiver 125 including the photomultiplier tube 127 is illustrated.

The photomultiplier tube 127 is located at a position where the reflected or scattered light is collected. For example, the photomultiplier tube 127 is opposite to the light emitter with respect to the semiconductor substrate W. Alternatively, the photomultiplier tubes 127 may be arranged around the light emitter 120. In the present embodiment, the photomultiplier tubes 127 are arranged at an angle of about 30° to about 60° with respect to the surface of the semiconductor substrate W. Also, the photomultiplier tubes 127 are inclined to the incident path of the light irradiated onto the semiconductor substrate W at an angle of about 10° to about 70°.

Defects of a minute structure on the semiconductor substrate W are inspected using either the reflected light or the scattered light. For example, light reflected from a region where the defects do not exist has a reflection angle substantially identical to an incident angle of the light. Light reflected from a region where the defects exist, however, has a reflection angle different from an incident angle of the light. Thus, when the reflection angle of the light is substantially identical to the incident angle of the light, the region onto which the light is irradiated does not have the defects so that the region is determined to be normal. When the reflection angle of the light is different from the incident angle of the light, however, the region onto which the light is irradiated have the defects so that the region is determined to be abnormal. As a result, the defects are recognized using either the reflected light or the scattered light. The scattered light is preferably used for inspecting the defects together with the reflected light.

A second polarizer 122 is placed between the light receiver 125 and the semiconductor substrate W. The second polarizer 122 includes a polarizing plate such as a plate having a ½ wavelength or a ¼ wavelength. The second polarizer 122 converts the scattered or reflected light into a polarized light such as a primary (P) polarized light, a secondary (S) polarized light, a circular (C) polarized light or a combination thereof.

The inspecting unit 150 is connected to the second polarizer 122. The inspecting unit 150 includes an analog/digital (A/D) converter 155, an image processor 160 and a defect classifier 165. The A/D converter 155 converts the light in the light receiver 125 into a digital signal. The image processor 160 converts the digital signal into image information. The defect classifier 165 classifies the detected defects based on each characteristic parameter corresponding to each inspection region, respectively.

The determining unit 130 includes an analyzer 135 and a memory 140. The analyzer 135 detects a variance of a light reflectivity at an interface between the inspection regions on which the minute structures are formed. The analyzer 135 selects a characteristic parameter among the entire characteristic parameters in the memory 140 that corresponds to an adjacent inspection region where the light reflectivity is changed. The analyzer 135 then provides the defect classifier 165 with the selected characteristic parameter.

Figure 5:
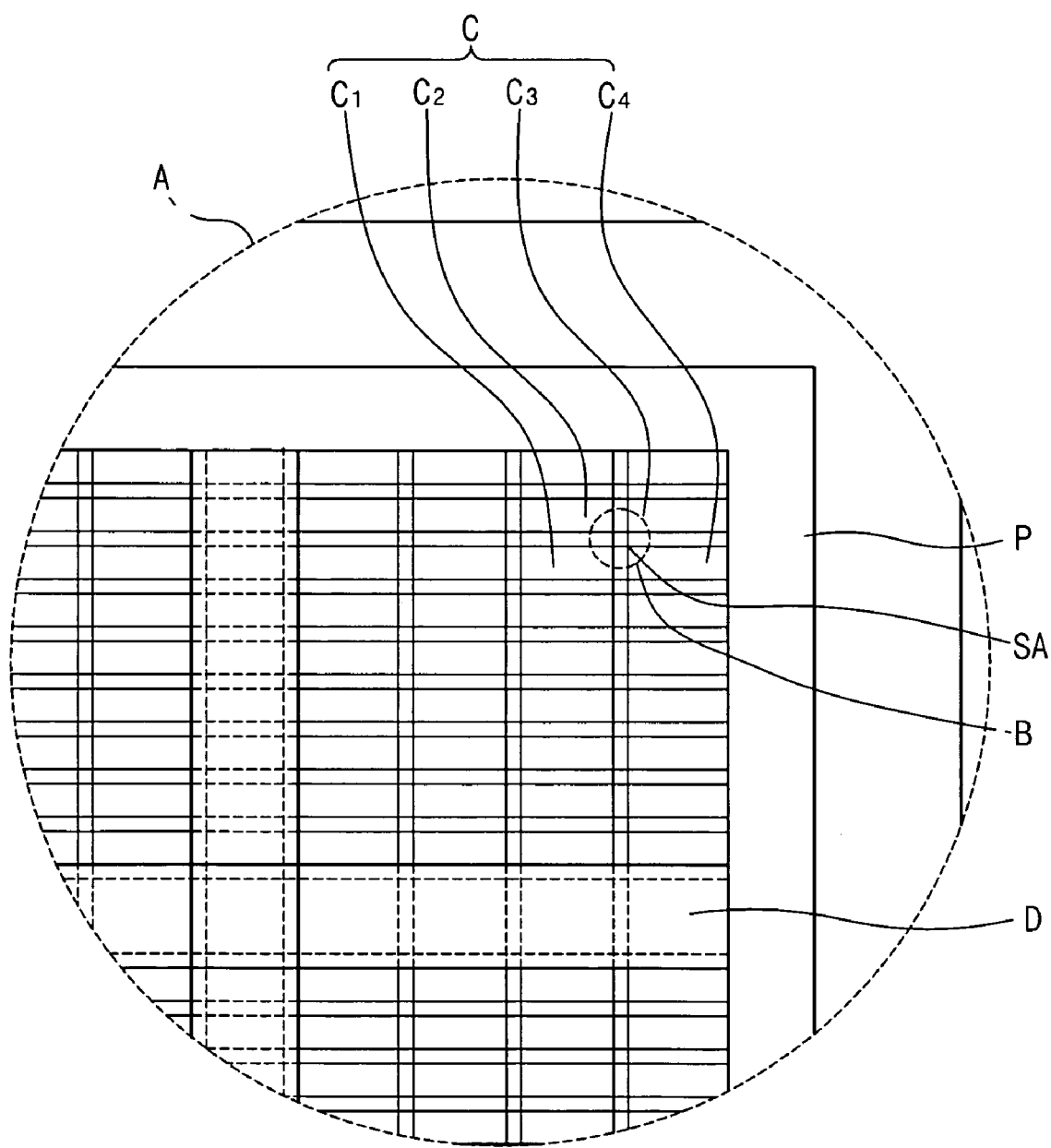
FIG. 5 is an enlarged plan view illustrating a die on the semiconductor substrate in FIG. 4.
Figure 6:
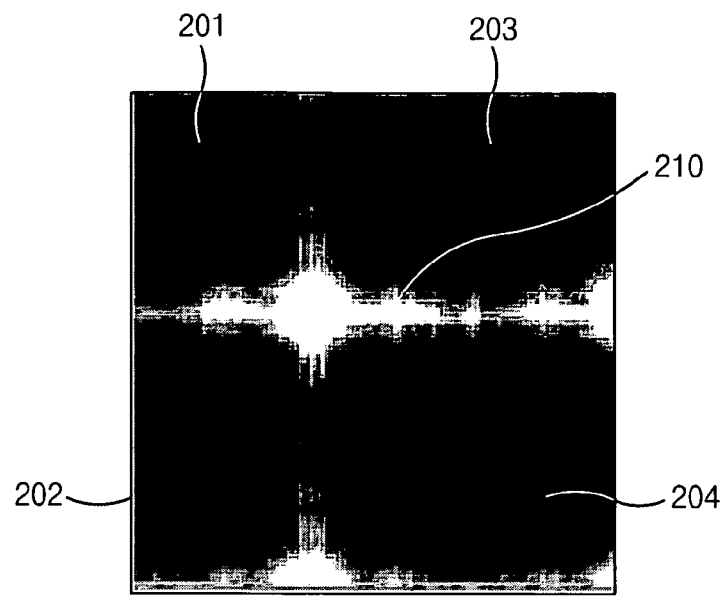
FIG. 6 is a picture illustrating a light reflectivity of a cell region and a sense amplifier (S/A) region in FIG. 5.
Figure 7:
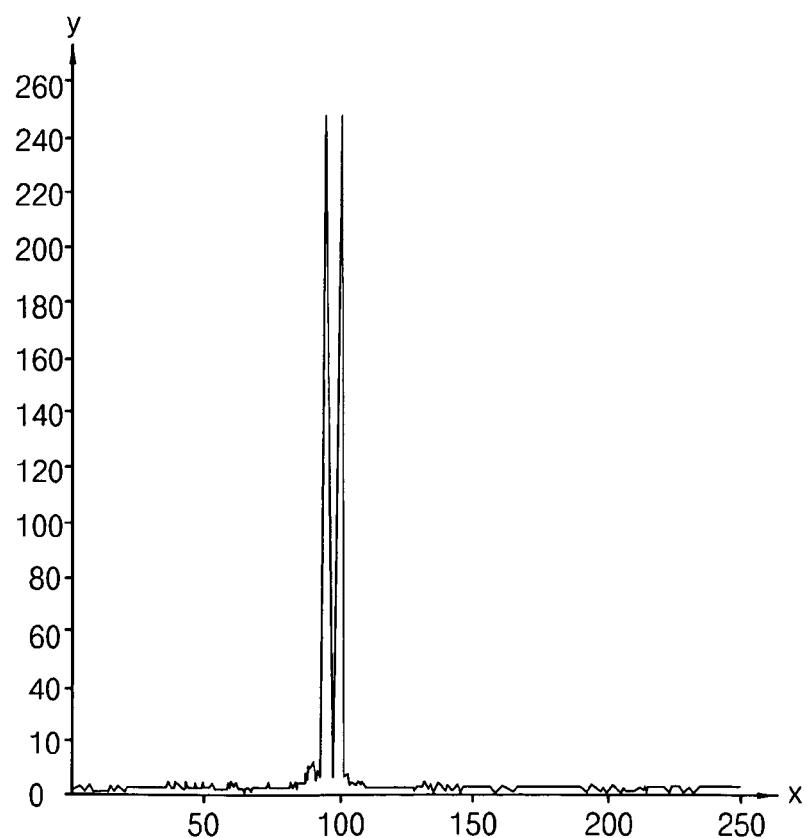
FIG. 7 is a graph illustrating a quantity of light collected in the cell region and the S/A region in FIG. 5.

FIG. 5 is an enlarged plan view of area A illustrating a die on the semiconductor substrate in FIG. 4. FIG. 6 is a picture illustrating light reflectivity of a cell region and a sense amplifier (S/A) region in FIG. 5. And FIG. 7 is a graph illustrating a quantity of a light collected in the cell region and the S/A region in FIG. 5.

Referring to FIGS. 4 to 7, a plurality of dies D is formed on the semiconductor substrate W. The dies D are divided into a cell region C, an S/A region SA, a peripheral region P, a decoder region D, etc. Minute structures are formed on each region, respectively. Memory circuits such as a transistor or a capacitor are formed in the cell region C. Amplification circuits for amplifying signals in the cell region C are formed in the S/A region SA, which is formed at a peripheral portion of the cell region C. Logic circuits for driving the memory circuits are formed in the peripheral region P that is formed at a peripheral portion of a semiconductor chip. Circuits through which the signals in the cell region C pass are formed in the decoder region D.

The semiconductor substrate W is scanned in a first direction with it being moved horizontally. Thus, the light is irradiated onto the semiconductor substrate W in a second direction substantially opposite to the first direction. The light receiver 125 of the scanning unit 110 collects the reflected or scattered light from the semiconductor substrate W. The light receiver 125 generates a current corresponding to a quantity of the collected light and then amplifies the current.

When the light is sequentially irradiated onto a first cell region C1 and the S/A region SA, in a sample region B, a picture in FIG. 6 is obtained. Here, a first region 201, a second region 202, a third region 203 and a fourth region 204 in FIG. 6 correspond to the first cell region C1, a second cell region C2, a third cell region C3 and a fourth cell region C4, respectively. Also, the S/A region SA in FIG. 5 corresponds to a boundary region surrounded by the first, second, third and fourth regions 201, 202, 203 and 204 in FIG. 6.

When quantities of the light collected from the cell region and the S/A region in FIG. 5 are represented as values, a graph in FIG. 7 is obtained. In FIG. 7, an x-axis indicates a horizontal coordinate on the semiconductor substrate W, and a y-axis represents the quantity of the light.

As shown in FIG. 7, a point 100 on the x-axis corresponds to the boundary region 210. A great amount of light is collected in the point 100 compared to other points on the x-axis. When the determining unit 130 is moved together with the stage 115, a point where the light is currently irradiated may be predicted based on the information provided from the light receiver 125.

The determining unit 130 detects the point where an inspection region is changed into another inspection region based on a difference between the quantities of the light by each region. In particular, the analyzer 135 of the determining unit 130 receives the information of the scattered or reflected light from the semiconductor substrate W from the light receiver 125 of the scanning unit 110. The analyzer 135 detects the difference between the quantities of the light among the information of the reflected or scattered light and then recognizes the point where the inspection region is changed into another inspection region. The analyzer 135 selects a characteristic parameter among characteristic parameters corresponding to another inspection region and then provides the inspection unit 150 with the selected characteristic parameter. Here, the characteristic parameters are predetermined and are also stored in the memory 140.

The characteristic parameters are obtained from inspecting a reference semiconductor substrate in a recipe setup step or a step preceding the recipe setup step. The reference semiconductor substrate is manufactured by a process substantially identical to that for forming the semiconductor substrate W. That is, the reference semiconductor substrate is substantially identical to the semiconductor substrate W.

The reference semiconductor substrate is scanned to obtain information of the reference semiconductor substrate. The information is converted into image information. The characteristic parameters of each region on the reference semiconductor substrate are set using a microscope, an SEM, a transmission electron microscope (TEM), etc., based on the image information.

The characteristic parameters are references for effectively classifying the defects on each region from the background signal. Examples of the characteristic parameters include contrast of the light irradiated onto the reference semiconductor substrate, intensity of the light, brightness of the light, a size of the minute structure or a combination thereof. Also, examples of the intensity include defect intensity, target intensity, reference intensity, difference intensity, etc. Further, examples of the size include an X-size, a Y-size, a log X/Y, a pixel, etc.

Diverse defects such as a groove, a scratch, an overhand, a particle, etc., may exist on the semiconductor substrate W. Defects may exist in concentration on a specific region of the semiconductor substrate W. Also, critical defects may exist on each region. The characteristic parameters are set considering the above-mentioned conditions.

Other characteristic parameters as well as the above-mentioned characteristic parameters may be used. The characteristic parameters may vary in accordance with the inspection object and an inspection apparatus. Thus, it is hard to illustrate all of the characteristic parameters. Since the characteristic parameters are selected in accordance with a skill or an experience of an inspector, it is also hard to limit a scope of the characteristic parameters. However, the characteristic parameters have been well known in documents so that persons skilled in the art may readily select the characteristic parameters.

The characteristic parameters may preferably include at least two selected from the contrast of the light, the defect intensity, the target intensity, the reference intensity, the difference intensity, the brightness of the light, the X-size, the Y-size, the log X/Y and the pixel. For example, when the defects detected on the cell region C are classified, the defect intensity and the reference intensity may be selected as the characteristic parameters. When the defects detected on the S/A region SA are classified, the target intensity and the difference intensity may be selected as the characteristic parameters. When the defects detected on the peripheral region P are classified, the intensity and the X-size may be selected as the characteristic parameters.

Further, different characteristic parameters may be used for a same region. Also, at least two characteristic parameters may be used for the same region. Persons skilled in the art may readily select the characteristic parameters corresponding to each region.

The set characteristic parameters are stored and managed in the memory 140. The set characteristic parameters include coordinate information and time information. The coordinate information corresponds to position information of a region on the semiconductor substrate W where a corresponding characteristic parameter is applied. The time information corresponds to information of the point where the inspection region is changed into another inspection region to be inspected based on another characteristic parameter.

The analyzer 135 recognizes the point where the inspection region is changed into another inspection region. The analyzer 135 also selects a characteristic parameter corresponding to the recognized point among the characteristic parameters in the memory 140 and then provides the inspecting unit 150 with the selected characteristic parameter.

The inspecting unit 150 inspects the information of the regions to detect the defects. The inspecting unit 150 classifies the defects based on the characteristic parameters provided from the determining unit 130. In particular, the A/D converter 155 converts the light in the light receiver 125 into the digital signal. The image processor 160 converts the digital signal into the image information. The defect classifier 165 detects the defects from the image information. The defect classifier 165 then classifies the detected defects based on the corresponding characteristic parameter.

That is, each region of the semiconductor substrate W is inspected based on at least one characteristic parameter that is set by inspecting a region of the reference semiconductor substrate having coordinates substantially identical to that of the region of the semiconductor substrate W.

Additionally, the determining unit 130 may control the light receiver 125 at the point where the inspection region is changed into another inspection region. For example, an optimal amplification ratio of the light receiver 125 corresponding to the point is predetermined. The amplification ratio is inputted into the light receiver 125 to obtain accurate information of each region on the semiconductor substrate W.

According to the above apparatus, the apparatus detects the defects and then classifies the defects without delay. That is, the defects are detected and classified without the semiconductor substrate W being moved to a reviewing apparatus.

Figure 8:
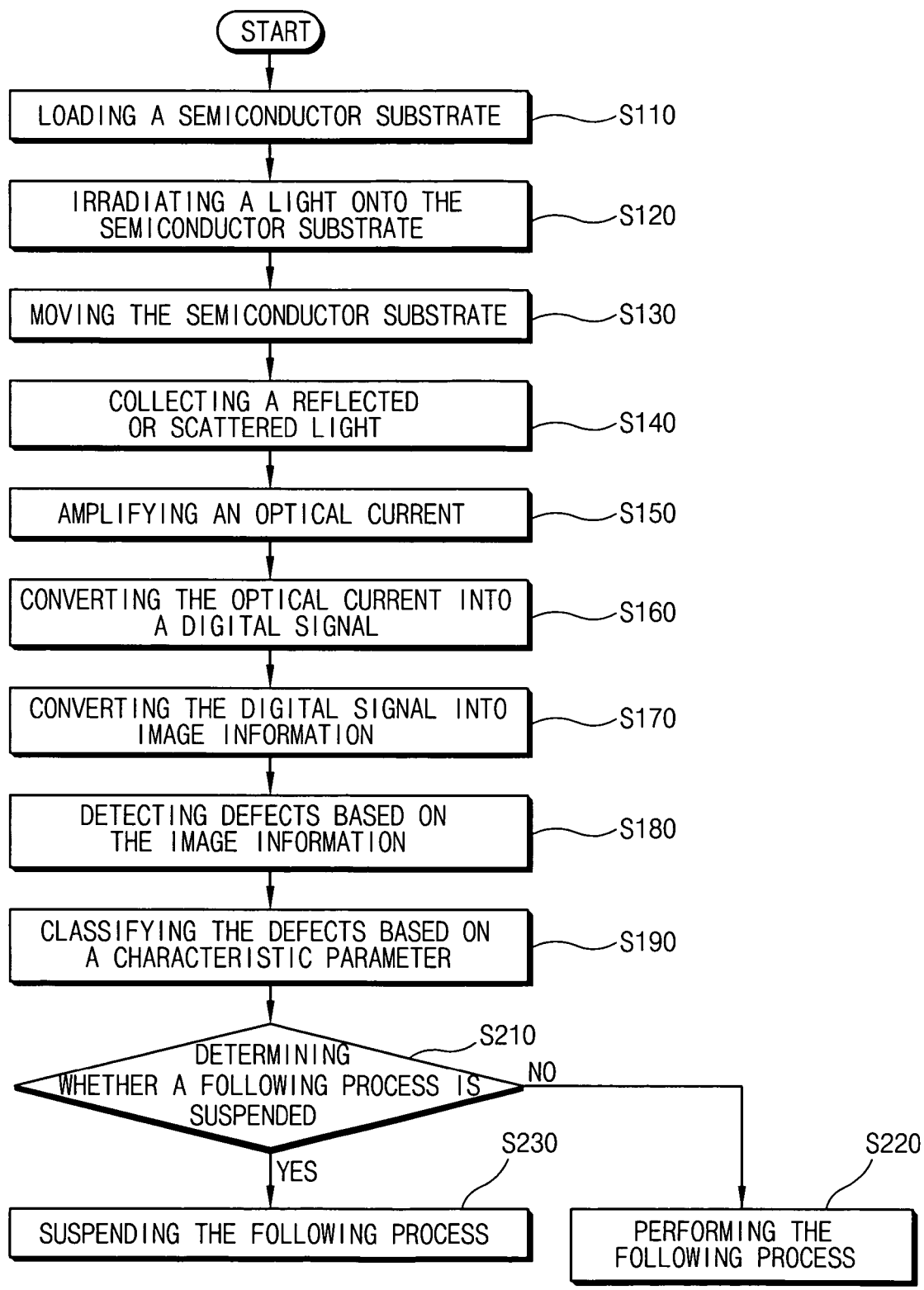
FIG. 8 is a flow chart illustrating a method of inspecting defects using the apparatus in FIG. 3.

FIG. 8 is a flow chart illustrating a method of inspecting defects using the apparatus in FIG. 3.

Referring to FIG. 8, in step S110, the semiconductor substrate is loaded into the apparatus. In step S120, the light is irradiated onto the semiconductor substrate. In step S130, the semiconductor substrate is moved. Here, the step S120 may be carried out simultaneously with the step S130.

In step S140, a light scattered or reflected from the semiconductor substrate is collected. In step S150, the optimal amplification ratio of the light receiver is obtained based on the collected scattered or reflected light. The optical current is then amplified by the amplification ratio. In step S160, the amplified optical current is converted into the digital signal. In step S170, the digital signal is converted into the image information. In step S180, the defects on a corresponding region are detected based on the image information. In step S190, the image information is inspected based on a characteristic parameter corresponding to the region to classify the defects.

Here, the characteristic parameters are obtained from inspecting a region of the reference semiconductor substrate that has coordinates substantially identical to that of the region on the semiconductor substrate. The characteristic parameters are references for effectively classifying the defects on each region from the background signal. Examples of the characteristic parameters include contrast of the light irradiated onto the reference semiconductor substrate, intensity of the light, brightness of the light, a size of the minute structure or a combination thereof. Also, examples of the intensity include defect intensity, target intensity, reference intensity, difference intensity, etc. Further, examples of the size include an X-size, a Y-size, a log X/Y, a pixel, etc.

The characteristic parameters are changed simultaneously with the point being determined. In step S210, whether a following process is performed or not is determined based on information of the classified defects.

When the classified defects are determined to be normal, in step S220, the following process is carried out. Otherwise, when the classified defects are determined to be abnormal, in step S230, the following process is suspended. An apparatus that is used in a preceding process, and one which potentially caused the defect, is then repaired.

Hereinafter, the method of inspecting defects is illustrated in detail.

In step S110, a light such as a laser having a wavelength of about 488 nm is irradiated onto at least two inspection regions on the semiconductor substrate on which the minute structures are formed. Here, the present invention is not restricted to a particular wavelength and kind of light.

In step S120, the light is irradiated onto the semiconductor substrate. In step S130, the semiconductor substrate is moved. Here, the step S120 may be carried out simultaneously with the step S130. Thus, the light is irradiated onto all of the regions on the semiconductor substrate.

In step S140, the light is reflected from the semiconductor substrate. Here, the reflected light may have a reflection angle substantially identical to the incident angle of the light. Alternatively, the light is scattered from the defects or the minute structures. The scattered or reflected light is collected. Here, the scattered or reflected light may be collected at a position that is inclined to the surface of the semiconductor substrate at an angle of about 30° to about 60° and to the incident direction of the light at an angle of about 10° to about 70° using the photomultiplier, a CCD camera, etc.

In step S150, the optimal amplification ratio of the light receiver is obtained based on the collected scattered or reflected light. The optical current is then amplified by the amplification ratio. Here, the optical current is generated from the light receiver such as the photomultiplier tube in accordance with an amount of the collected light.

In general, a region where the minute structures are formed has a light reflectivity different from that of a boundary region between the regions having the minute structures. Thus, intensities of the optical currents generated from each region are different from each other. As a result, the point where the inspection region is changed into another inspection region is recognized based on the different intensities of the optical currents. The characteristic parameter is then changed into a new one corresponding to the changed inspection region. In the present embodiment, this step is carried out simultaneously with the reflected or scattered light being collected. Thus, this step is not illustrated in FIG. 8.

The characteristic parameters are obtained from inspecting a reference semiconductor substrate in a recipe setup step or a step preceding the recipe setup step. The reference semiconductor substrate is scanned to obtain information of the reference semiconductor substrate. The information is converted into image information. The characteristic parameters of each region on the reference semiconductor substrate are set using a microscope, an SEM, a transmission electron microscope (TEM), etc., based on the image information.

In step S160, the amplified optical current is converted into the digital signal.

In step S170, the digital signal is converted into the image information.

In step S180, the defects on a corresponding region are detected based on the image information.

In step S190, the image information is inspected based on a characteristic parameter corresponding to the region to classify the defects. That is, the defects on each region are classified based on a characteristic parameter, which is obtained from inspecting a region of the reference semiconductor substrate that has coordinates substantially identical to that of the region on the semiconductor substrate. Here, the defects may be effectively classified without the semiconductor substrate being moved to an inspection apparatus such as an SEM or a TEM.

In step S210, whether a following process is performed or not is determined based on information of the classified defects. That is, performing the following process is dependent on the number of the defects and critical defects. This determination is readily obtained from the classified defects.

When the classified defects are determined to be normal, in step S220, the following process is carried out. That is, when the number of the defects is within an allowable number or the critical defects do not exist, the following process is performed.

On the contrary, when the classified defects are determined to be abnormal, in step S230, the following process is suspended. That is, when the number of the defects is beyond the allowable number or the critical defects exist, the following process is suspended. An apparatus that is used in a preceding process is then repaired.

According to the present embodiment, a method of inspecting defects may have improved efficiency so that a process for reviewing defects may be omitted. Thus, the inspection process may be automatically carried out.

According to the present invention, the defects are inspected based on the characteristic parameters corresponding to each inspection region on an object so that the detected defects may be accurately classified. Thus, a time and a cost for unnecessarily reviewing defects may be remarkably reduced. Also, the inspection apparatus may have improved reliability so that the inspection apparatus may be automatically operated.

Having described the preferred embodiments of the present invention, it is noted that modifications and variations can be made by persons skilled in the art in light of the above teachings. It is therefore to be understood that changes may be made in the particular embodiment of the present invention disclosed which is within the scope and the spirit of the invention outlined by the appended claims.

What is claimed is:

1. A method of inspecting defects, comprising:
    preparing an actual object that is divided into at least two actual regions;
    inspecting a first actual region among the actual regions based on a first characteristic parameter;
    determining a point where an actual inspection region is changed from the first actual region into a second actual region adjacent to the first actual region;
    responsive to the determining step, changing from the first characteristic parameter to a second characteristic parameter;
    inspecting the second actual region based on the second characteristic parameter; and
    classifying defects found in the first and second regions based on the inspecting steps,
    wherein the first and second characteristic parameters are selected from a group consisting of a contrast of a light that is reflected from a reference object an intensity of the light, a brightness of the light, a size of a minute structure on the reference object or a combination thereof.

2. The method of claim 1, further including:
    inspecting first and second reference defects on a first and second reference region, respectively, of a reference object;
    obtaining the first and second characteristic parameters based on first and second reference defect inspections, respectively.

3. The method of claim 2, wherein the first reference region of the reference object has first coordinates substantially identical to that of the first actual region of the actual object, and the second reference region of the reference object has second coordinates substantially identical to that of the second actual region of the actual object.

4. The method of claim 1, wherein determining the point comprises detecting a variance of a light reflectivity at a boundary region between the first and second actual regions.

5. The method of claim 1, wherein inspecting the first actual region comprises:
    irradiating a light onto the first actual region;
    collecting a light reflected or scattered from the first actual region;
    converting the collected light into a first image signal;
    detecting defects on the first actual region based on the first image signal; and
    classifying the detected defects based on the first characteristic parameter.

6. The method of claim 5, wherein irradiating the light comprises:
    polarizing the light into a polarized light; and
    irradiating the polarized light onto the first actual region.

7. The method of claim 6, wherein the polarized light comprises at least one selected from the group consisting of a primary (P) polarized light, a secondary (S) polarized light and a circular (C) polarized light.

8. The method of claim 5, wherein collecting the light comprises:
polarizing the reflected or scattered light into a return polarized light; and
collecting the return polarized light.

9. The method of claim 8, wherein the return polarized light comprises at least one selected from the group consisting of a primary (P) polarized light, a secondary (S) polarized light and a circular (C) polarized light.

10. The method of claim 1, wherein inspecting the second actual region comprises:
irradiating a light onto the second actual region;
collecting a light reflected or scattered from the second actual region;
converting the collected light into a second image signal;
detecting defects on the second actual region based on the second image signal; and
classifying the detected defects based on the second characteristic parameter.

11. The method of claim 1, wherein the actual object comprises a semiconductor substrate, and the first and second actual regions comprise two different regions, respectively, selected from the group consisting of a cell region, a sense amplifier region, a peripheral region and a decoder region.

12. An apparatus for inspecting defects, comprising:
a scanning unit for scanning an actual object, which is divided into at least two actual regions, using a light to obtain information of the actual regions;
a determining unit for determining a point where an inspection region is changed into another inspection region adjacent to the inspection region; and
an inspecting unit for inspecting the information of the inspection region based on at least one of a plurality of characteristic parameters stored in a memory, which corresponds to the inspection region, to detect and classify defects on the inspection region, said determining unit including an analyzer for selecting the at least one of the plurality of characteristic parameters and providing the inspecting unit with the selected characteristic parameter,
wherein the characteristic parameter comprises a contrast of a light that is reflected from a reference object, an intensity of the light, a brightness of the light, a size of a minute structure on the reference object or a combination thereof.

13. The apparatus of claim 12, wherein the inspecting unit comprises:
an A/D converter for converting the information of the actual regions into a digital signal;
an image processor for converting the digital signal into image information; and
a defect classifier for inspecting the image information based on the characteristic parameter to detect and classify the defects.

14. The apparatus of claim 13, wherein the inspecting unit further comprises a memory for storing the characteristic parameter.

15. The apparatus of claim 12, wherein the scanning unit comprises:
a stage for supporting and transferring the actual object;
a light emitter for irradiating the light onto the actual object; and
a light receiver for collecting a light scattered from the actual object and for amplifying the collected light by an amplification ratio.

16. The apparatus of claim 15, wherein the light receiver comprises a photomultiplier tube or a charge-coupled device (CCD) camera.

17. The apparatus of claim 15, wherein the scanning unit further comprises:
a first polarizer positioned between the light emitter and the actual object to convert the light into a first polarized light; and
a second polarizer positioned between the object and the light receiver to convert a light reflected or scattered from the object into a second polarized light.

18. A method for inspecting defects on a semiconductor substrate, comprising:
illuminating a first irradiation point on the semiconductor substrate located within a first region of the semiconductor substrate;
collecting light from the first irradiation point; analyzing the collected light based on a first characteristic parameter associated with the first region and determining whether an abnormal defect exists at the first irradiation point based on the analyzing step;
moving the irradiation point to second irradiation point located within a second region of the semiconductor substrate and collecting light from the second irradiation point; and
analyzing the collected light from the second irradiation point based on a second characteristic parameter, different from the first characteristic parameter, associated with the second region and determining whether an abnormal defect exists at the second irradiation point based on the second analyzing step,
wherein the first and second characteristic parameters are selected from the group consisting of a contrast of a light that is reflected from a reference object, an intensity of the light, a brightness of the light, a size of a minute structure on the reference object or a combination thereof.

19. The method of claim 18, wherein the first and second characteristic parameters include at least two selected from the group consisting of the contrast of the light, the defect intensity, the target intensity, the reference intensity, the difference intensity, the brightness of the light, the X-size, the Y-size, the log X/Y and the pixel.

20. The method of claim 19, further including associating the defect intensity and the reference intensity with the first characteristic parameter when the first region is a cell region.

21. The method of claim 19, further including associating the target intensity and difference intensity with the first characteristic parameter when the first region is an S/A region.

22. The method of claim 19, further including associating the target intensity and the X-size with the first characteristic parameter when the first region is a peripheral region.

23. The method of claim 19, further including associating a plurality of different characteristic parameters with the same region.

24. The method of claim 18, wherein the first region is a cell region and the first characteristic parameter is a contrast, and the second region is a peripheral region and the second characteristic parameter is an intensity.

* * * * *

UNITED STATES PATENT AND TRADEMARK OFFICE
CERTIFICATE OF CORRECTION

PATENT NO. : 7,433,032 B2 Page 1 of 1
APPLICATION NO. : 11/253028
DATED : October 7, 2008
INVENTOR(S) : Joung-Soo Kim et al.

It is certified that error appears in the above-identified patent and that said Letters Patent is hereby corrected as shown below:

Column 13, line 18, the word "classifying" should read -- classifying --.

Signed and Sealed this

Seventeenth Day of February, 2009

JOHN DOLL
*Acting Director of the United States Patent and Trademark Office*